United States Patent [19]
McGee et al.

[11] Patent Number: 5,166,756
[45] Date of Patent: Nov. 24, 1992

[54] POWDER FIBER OPTIC PROBE HAVING ANGLED END IN NIR OPTICAL ANALYZING INSTRUMENT

[75] Inventors: Philip A. McGee, Beltsville, Md.; Kenneth P. VonBargen, Berwyn Heights, Md.

[73] Assignee: NIR Systems Incorporated, Silver Spring, Md.

[21] Appl. No.: 619,047

[22] Filed: Nov. 28, 1990

[51] Int. Cl.$^5$ .................... G01N 21/31; G01N 21/47
[52] U.S. Cl. ................................ 356/446; 250/227.29
[58] Field of Search ............... 356/446, 445; 250/576, 250/227.29

[56] References Cited

U.S. PATENT DOCUMENTS

| | | | |
|---|---|---|---|
| 4,180,331 | 12/1979 | Lundstrom | 356/445 |
| 4,449,535 | 5/1984 | Renault | 350/96.29 X |
| 4,737,006 | 4/1988 | Warbrick | 356/73.1 X |
| 4,753,530 | 6/1988 | Knight et al. | 356/73 |

Primary Examiner—Vincent P. McGraw

[57] ABSTRACT

In an optical instrument for infrared spectral analysis of powder, an improved fiber optic probe is provided. Fiber optics carry light to and from the probe and the fiber optics terminate in the probe in a fiber optic endface. A sapphire rod is positioned to abut the fiber optic endface. The sapphire rod has a distal endface arranged at slightly less than one-half the maximum acceptance angle of the optic fibers in the probe.

21 Claims, 1 Drawing Sheet

POWDER FIBER OPTIC PROBE HAVING ANGLED END IN NIR OPTICAL ANALYZING INSTRUMENT This invention relates to an instrument for infrared spectral analysis of powder and, more specifically, to such an instrument with an improved probe for immersing in bulk powder to measure the reflectivity of the powder in the infrared range.

BACKGROUND OF THE INVENTION

A powerful technology for analyzing matter involves measuring the reflectance from or the transmission through the matter to be analyzed at narrow band wavelengths in the near infrared range known as NIR. To carry out such analysis, the matter is irradiated with NIR light and the amount of light transmitted through or reflected from the matter at narrow band wavelengths is measured and analyzed. Instruments for making such measurements are disclosed in U.S. Pat. Nos. 4,264,205 and 4,285,596 to Isaac J. Landa and U.S. Pat. No. 4,040,747 to Donald R. Webster. When the matter to be analyzed is in the form of bulk powder, the reflectivity of the powder can be measured by means of a probe immersed in the powder. Infrared light is transmitted to the probe by fiber optics and infrared light reflected from the powder to the probe is carried to a photodetecting analysis system. Normally, the restriction of the light to narrow band wavelengths is achieved by transmitting a narrow band wavelength of light to the powder and scanning the center frequency of the narrow band wavelength through the near infrared spectrum. Alternatively, a wide band of near infrared light could be transmitted to the probe and the received light could be subjected to separation into narrow band components. The use of the probe to analyze the powder in a manner as described above is not fully satisfactory because a substantial amount of the infrared light is specularly reflected from the powder and received by the probe. The specularly reflected light interferes with accurate analysis of the powder.

SUMMARY OF THE INVENTION

The present invention provides a probe which substantially eliminates specularly reflected light from the light received by the optic fibers in the probe. In accordance with the invention, the fiber optics in the probe terminate in a planar endface. Abutting the planar endface is an NIR transmissive rod, which has a distal planar endface inclined at an angle to the plane of the endface of the fiber optics. The angle of the rod endface relative to the fiber optic endface is slightly less than one-half the maximum acceptance angle of the optic fibers in the fiber optic endface. When the probe is immersed in powder, the granules of powder irradiated by light from the probe will abut the window at the angle of the rod endface. This arrangement has the effect of substantially eliminating specularly reflected light from the light received by the receiving optic fibers in the endface of the fiber optic cable. In this manner, the problem caused by specularly reflected light in the light reflected from the powder is avoided.

DESCRIPTION OF THE PREFERRED EMBODIMENT

Figure 1:
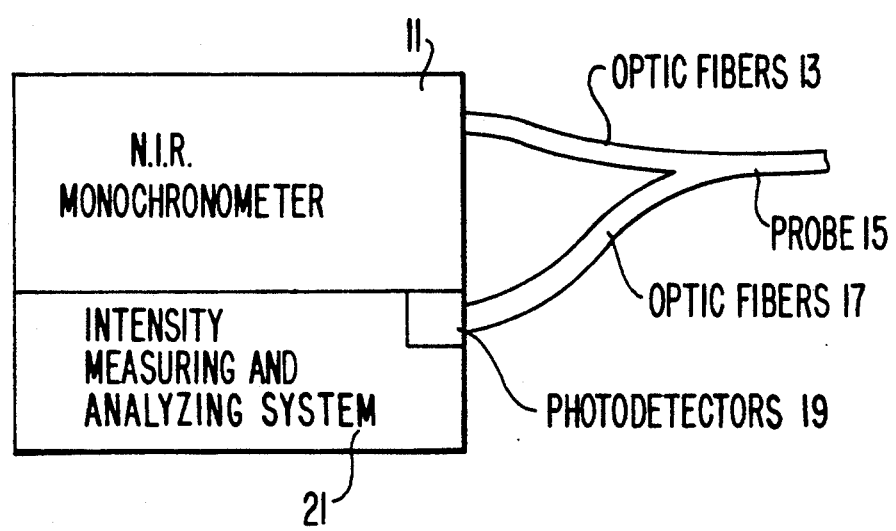
FIG. 1 schematically illustrates the system of the present invention.

As shown in the invention, an NIR monochrometer 11 transmits narrow band infrared light through a flexible fiber optic cable 13 to a probe 15. The infrared monochrometer may be an instrument such as disclosed in copending application Ser. No. 07/294,679, filed Jan. 9, 1989, now U.S. Pat. No. 4,969,739, invented by Philip A. McGee and assigned to the assignee of the present invention. The NIR monochrometer described in the above-identified application comprises an oscillating grating which distributes light from a light source into its spectral components. As the grating oscillates, it scans the center wavelength of a narrow band of infrared light transmitted through an exit slit. The entrance end of the fiber optic cable 13 is shaped in the form of the exit slit of the monochrometer 11 and is arranged to receive the near infrared light transmitted through the exit slit of the near infrared monochrometer. Instead of using an oscillating grating, the narrow band wavelength could be provided by an interference filter or filters in the center wavelength scanned by tilting the filters. Alternatively, discrete narrow band wavelengths can be provided by light emitting diodes.

The optic fibers of the fiber optic cable 13 are combined in the probe 15 with optic fibers from a flexible fiber optic cable 17, which is used to carry reflected light received by the probe back to photodetectors 19. The photodetectors 19 convert the received light into an electrical signal having an amplitude corresponding to the intensity of the received light. The photodetectors 19 are part of an intensity measuring and analyzing system 21 which measures the amplitude of the output signal from the photodetectors thereby providing a measurement of the intensity of the light received by the photodetectors and reflected from a powder at the window 23. The amplitude values measured in this manner are then used to analyze the powder by the analyzing system, such as in the manner disclosed in the Webster U.S. Pat. No. 4,040,747.

Figure 2:
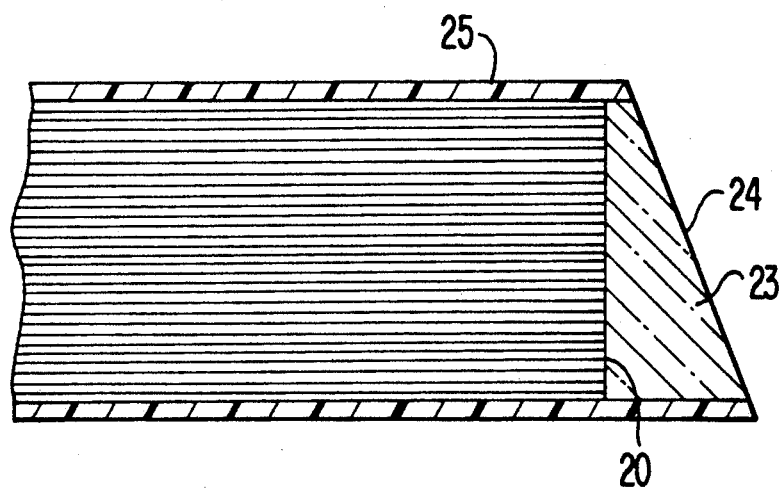
FIG. 2 is an axial sectional view taken through the fiber optic probe of the system of the invention.

In the probe 15, as shown in FIG. 2, the emitting ends of the optic fibers of the fiber optic cable 13 and the receiving ends of the optic fibers of the fiber optic cable 17 are arranged in a planar endface 20 in which the optic fibers of the cable 13 and the optic fibers of the cable 17 are randomly distributed among each other. Alternatively, the fibers may be arranged so that the transmitting fibers are formed into a central circle surrounded by a ring of the receiving fibers or vice versa. The number of the transmitting fibers is limited to the number which can be positioned to accept light at the exit slit at the monochrometer. There will be about twice as many receiving fibers in the probe 15 as there are transmitting fibers. The plane of the endface on which the ends of the optic fibers are distributed is arranged perpendicular to the axis of the fibers at the endface. Mounted in the probe is a window in the form of a rod 23 made of material transparent to NIR light, such as sapphire. The rod 23 is centered on the axis of the probe 15 and has a distal endface 24 an angle to plane of the fiber optic endface 20. Preferably the angle between the endface 24 and the endface 20 is slightly less than one-half the maximum acceptance angle of the receiving optic fibers in the probe 15. A typical maximum acceptance angle for optic fibers is just under 50 degrees which would mean that the angle of the endface 24 should be 25 degrees. This means that the axes of the optic fibers at the endface 20 would make an angle of 25 degrees to perpendicular to the plane of the endface 24 for such receiving optic fibers. The probe 15 is provided with a sheath 25, which confines the transmitting and receiving ends of the optic fibers at the endface 20 and also mounts the rod 23 in abutment with the endface 20. Index of refraction matching oil is provided between the internal endface of the rod 23 which abuts the endface 20 in order to provide efficient transmission between the optic fibers and the rod 23.

When the probe as described above is immersed in a container containing bulk powder, specularly reflected light received by the optical fibers of cable 17 is substantially eliminated. If the angle of the endface 24 is made substantially less than one-half the maximum acceptance angle, the amount of specularly reflected light received by the optic fibers of the cable 17 is reduced, but will not be reduced as much as with a window at slightly less than one-half the maximum acceptance angle. The amount of specularly reflecting light received by the optic fibers of the cable 17 decreases as the angle increases toward the maximum acceptance angle. If the angle of the endface 24 is increased to angles greater than one-half the maximum acceptance angle, no further reduction in the specularly reflected light is achieved. The reason for the reduction in the specularly reflected light in the angled endface 24 is not known for certain, but it is believed that the specularly reflecting surfaces of the granules of the powder align themselves with the endface 24 so that the light reflected from these planes of powder is reflected at an angle twice the angle of the endface 24 relative to the axes of the receiving ends of the fibers of the cable 17. If the maximum acceptance angle of the receiving fibers is just under fifty degrees so that the endface 24 is at 25 degrees, the specularly reflected light will be reflected at 50 degrees, just beyond the limit of acceptance for the receiving ends of the optic fibers. Thus, by the endface 24 orienting the specularly reflecting planes of the powder at 25 degrees, the specularly reflected light is reflected to the receiving ends of the optic fibers of the cable 17 outside of the maximum acceptance angle.

It will be apparent that the endface 24 could be arranged at an angle of substantially less than one-half the maximum acceptance angle, but to achieve the maximum elimination of specularly reflected light, the endface 24 should be angled at an angle just greater than one-half the maximum acceptance angle of the receiving optic fibers. The endface 24 can be angled at angles substantially greater than one-half the maximum acceptance angle with respect to the endface 20, but the preferred angle for the endface 24 is slightly greater than one-half the maximum acceptance angle to provide a more convenient shape for the end of the probe and also to not increase more than necessary the difference in the distances of the granules of powder at the endface 24 over different parts of the endface 24 from the endface 20.

Instead of employing a sapphire rod to define the endface 24, a sapphire windowpane mounted at the required angle in the probe could be employed to provide the required angle on the distal endface of the probe.

When the transmitting and receiving fibers are separated into concentric circular arrays instead of being randomly distributed among each other, the minimum axial length of the sapphire rod should be ⅜th of an inch to permit the diffusely reflected light from the powder granules to reach the receiving optic fibers of the probe. When the transmitting and receiving fibers are randomly distributed among each other, the minimum axial length of the rod 23 may be as short as practical.

The above description is of a preferred embodiment of the invention and modifications in addition to those mentioned above may be made thereto without departing from the spirit and scope of the invention which is defined in the appended claims.

We claim:

1. An optical probe comprising a window transparent to light and defining a planar exterior surface, a fiber optic cable comprising a multiplicity of optical fibers having distal ends mounted at said window arranged to transmit light through said window and to receive light reflected back through said window, said optical fibers having parallel axes displaced from perpendicular to said planar surface by an angle at approximately one-half the maximum acceptance angle of said optical fibers.

2. An optical probe as recited in claim 1, wherein said fiber optic cable is flexible.

3. An optical measuring instrument comprising a optical probe as recited in claim 1, further comprising light source means for introducing light into a first set of said optical fibers to be emitted from the distal ends of such optical fibers to irradiate material in contact with the exterior surface of said window.

4. A measuring instrument as recited in claim 3, wherein the distal ends of a second set of said optical fibers are receiving ends mounted in said probe positioned to receive light reflected through said planar exterior surface by material in contact with said planar exterior surface.

5. An optical measuring instrument as recited in claim 4, wherein said distal ends are arranged in a planar endface positioned at an angle to said planar exterior surface.

6. A measuring instrument as recited in claim 5, wherein the distal ends of said first set of optical fibers and the distal ends of said second set of optical fibers are randomly distributed among each other in said endface.

7. An optical measuring instrument as recited in claim 5, wherein said window comprises a transparent rod having an internal endface abutting said planar endface, the planar exterior surface of said window comprising a distal endface of said rod.

8. An optical measuring instrument as recited in claim 4, wherein light receiving by said optical fibers from said light source means at any given instant of time consists of a narrow band wavelength, and wherein said light source means comprises means to vary the center frequency of said narrow band wavelength.

9. An optical measuring instrument as recited in claim 8, wherein said light source means comprises a monochrometer operable to scan the center frequency of said narrow band wavelength through a range of frequencies.

10. An optical measuring instrument as recited in claim 4, further comprising photodetecting means to detect and measure the intensity of light reflected back through said window and received by said second set of optical fibers and transmitted through said second set of optical fibers.

11. A method of measuring the reflectance of powder comprising:

inserting into the powder an optical probe having a window which is transparent to light and which defines an exterior planar surface to align planar surfaces of said powder abutting said window with said window;

transmitting light through said window and said exterior planar surface and into said powder;

receiving through at least one optical fiber having a receiving end mounted in said probe light diffusely reflected back through said planar exterior surface by powder in contact with said planar exterior surface while excluding transmission through said optical fiber light specularly reflected from said planar surfaces 12. A method according to claim 11, wherein the step of receiving comprises receiving the reflected light through a multiplicity of optical fibers having ends mounted in the probe while excluding transmission from said multiplicity of optical fibers light specularly reflected from said planar surfaces of said powder.

13. A method according to claim 11, wherein the step of transmitting light comprises transmitting light through at least one second optical fiber having an emitting end mounted in the probe, wherein the emitting end has an axis parallel to the axis of said receiving end.

14. A method according to claim 12, further comprising transmitting light though a multiplicity of optical fibers having emitting ends with axes parallel to the axes of said receiving ends.

15. A method according to claim 14, wherein the steps of transmitting and receiving are done through optical fibers having ends arranged in a planar endface positioned at an angle to the planar exterior surface.

16. A method according to claim 13, wherein the light is transmitted from the emitting end, through a transparent rod having an internal endface abutting the endface of the transmitting optical fiber, including transmitting the light through a distal endface of the rod, which is the planar exterior surface of the window.

17. The method according to claim 11, wherein the step of transmitting comprises transmitting only a narrow band wavelength.

18. The method according to claim 17, wherein the step of transmitting comprises varying the center frequency of the narrow band wavelength.

19. The method according to claim 18, wherein the step of transmitting comprising scanning the center frequency of the narrow band wavelength through a range of frequencies.

20. A method according to claim 11, further comprising detecting and measuring the intensity of light received by the receiving ends.

21. A method according to claim 11, comprising receiving the light through an optical fiber having a receiving end with an axis at an angle of slightly less than one-third the maximum acceptance angle of the optic fiber.

* * * * *

UNITED STATES PATENT AND TRADEMARK OFFICE
CERTIFICATE OF CORRECTION

PATENT NO. : 5,166,756
DATED : November 24, 1992
INVENTOR(S) : Philip A. McGee et al.

It is certified that error appears in the above-identified patent and that said Letters Patent is hereby corrected as shown below:

Column 5, claim 11, line 14, after "surfaces", insert --of said powder.--.

Signed and Sealed this

Nineteenth Day of October, 1993

Attest:

BRUCE LEHMAN

*Attesting Officer*     *Commissioner of Patents and Trademarks*